(12) United States Patent
Barchas et al.

(10) Patent No.: US 6,297,414 B1
(45) Date of Patent: Oct. 2, 2001

(54) DEEP SELECTIVE HYDROGENATION PROCESS

(75) Inventors: Richard Barchas, Houston, TX (US); Peter Bell, Scotland (GB)

(73) Assignee: Stone & Webster Process Technology, Inc., Houston, TX (US)

( * ) Notice: Subject to any disclaimer, the term of this patent is extended or adjusted under 35 U.S.C. 154(b) by 0 days.

(21) Appl. No.: 09/415,114

(22) Filed: Oct. 8, 1999

(51) Int. Cl.$^7$ ................ C07C 5/05; C07C 5/08; C07C 7/10
(52) U.S. Cl. ............... 585/259; 585/809; 585/844; 585/845; 585/846
(58) Field of Search ............... 585/259, 844, 585/845, 846, 809

(56) References Cited

U.S. PATENT DOCUMENTS

| | | | |
|---|---|---|---|
| 1,875,924 | 9/1932 | Horsley . | |
| 2,077,041 | 4/1937 | Davis et al. | 260/170 |
| 2,363,309 | 11/1944 | Friedman et al. | 260/677 |
| 2,377,221 | 5/1945 | Francis et al. | 260/669 |
| 2,391,404 | 12/1945 | Friedman et al. | 260/677 |
| 2,471,550 | 5/1949 | Shaw | 260/677 |
| 2,515,140 | 7/1950 | Strand | 260/677 |
| 2,913,505 | 11/1959 | Van Raay et al. | 260/677 |
| 3,101,381 | 8/1963 | Baxter | 260/677 |
| 3,189,658 | 6/1965 | Quinn | 260/666 |
| 3,395,192 | 7/1968 | Long | 260/677 |
| 3,676,516 | 7/1972 | Haskell et al. | 260/677 |
| 3,679,763 | 7/1972 | Livingston | 260/677 |
| 3,756,036 | 9/1973 | Ezell | 62/28 |
| 3,758,603 | 9/1973 | Steigelmann et al. | 260/677 |
| 3,758,605 | 9/1973 | Hughes et al. | 260/677 |
| 3,763,200 | 10/1973 | Dines | 260/430 |
| 3,770,842 | 11/1973 | Steigelmann et al. | 60/677 |
| 3,773,844 | 11/1973 | Perry et al. | 260/669 |
| 3,787,514 | 1/1974 | Bernusset | 260/677 |
| 3,864,418 | 2/1975 | Hughes et al. | 260/677 |
| 3,865,890 | 2/1975 | Steigelmann et al. | 55/16 |
| 3,944,628 | 3/1976 | Suzuki et al. | 260/674 |
| 4,014,665 | 3/1977 | Steigelmann | 55/16 |
| 4,025,574 | 5/1977 | Tabler et al. | 260/277 |
| 4,060,566 | 11/1977 | Yahnke | 260/677 |
| 4,105,588 | 8/1978 | Balducci et al. | 252/454 |
| 4,121,917 | 10/1978 | Baker et al. | 62/28 |
| 4,132,744 | 1/1979 | Knifton | 260/677 |
| 4,154,770 | 5/1979 | Kaplan | 585/332 |
| 4,174,353 | 11/1979 | Marcinkowsky et al. | 585/835 |
| 4,235,983 | 11/1980 | Steigelmann et al. | 526/68 |
| 4,328,382 | 5/1982 | Alter et al. | 585/844 |
| 4,347,392 | 8/1982 | Cosyns et al. | 585/259 |
| 4,398,052 | 8/1983 | Tabler et al. | 585/845 |
| 4,409,410 | 10/1983 | Cosyns et al. | 585/259 |
| 4,484,015 | 11/1984 | Johnson et al. | 585/262 |
| 4,525,180 | 6/1985 | Hirai et al. | 55/37 |
| 4,546,094 | 10/1985 | Hirai et al. | 502/402 |
| 4,571,442 | 2/1986 | Cosyns et al. | 585/261 |
| 4,652,280 | 3/1987 | Boeren et al. | 55/67 |
| 4,747,855 | 5/1988 | Hirai et al. | 55/74 |
| 4,762,956 | 8/1988 | Liu et al. | 585/259 |
| 4,826,603 | 5/1989 | Hayes, Jr. et al. | 210/635 |
| 4,864,071 | 9/1989 | Hirai et al. | 585/829 |
| 4,943,673 | 7/1990 | Norman et al. | 585/845 |
| 5,015,268 | 5/1991 | Ho | 55/16 |
| 5,057,641 | 10/1991 | Valus et al. | 585/818 |
| 5,059,732 | 10/1991 | Cosyns et al. | 585/259 |
| 5,062,866 | 11/1991 | Ho | 55/16 |
| 5,090,977 | 2/1992 | Strack et al. | 62/23 |
| 5,191,151 | 3/1993 | Eriksen et al. | 585/818 |
| 5,191,153 | 3/1993 | Cymbaluk et al. | 585/833 |
| 5,202,521 | 4/1993 | Brown et al. | 585/848 |
| 5,326,929 | 7/1994 | Mehra et al. | 585/809 |
| 5,365,011 | 11/1994 | Ramachandran et al. | 585/829 |
| 5,452,581 | 9/1995 | Dinh et al. | 62/24 |
| 5,510,550 | 4/1996 | Cheung et al. | 585/259 |
| 5,516,851 | 5/1996 | Flick et al. | 525/330.2 |
| 5,516,966 | 5/1996 | Nowack et al. | 585/848 |
| 5,523,512 | 6/1996 | Cymbaluk et al. | 585/848 |
| 5,859,304 | 1/1999 | Barchas et al. | 585/809 |

FOREIGN PATENT DOCUMENTS 9404477   3/1994   (WO) ................ C07C/5/03

Primary Examiner—Walter D. Griffin
Assistant Examiner—Tam M. Nguyen
(74) Attorney, Agent, or Firm—Hedman & Costigan, P.C

(57) ABSTRACT

The present invention provides an improved method for deep selective hydrogenation for use in recovering high purity olefins from cracked gas effluents or other paraffin/olefin gaseous mixtures by use of a chemical absorption process.

40 Claims, 4 Drawing Sheets

US 6,297,414 B1

DEEP SELECTIVE HYDROGENATION PROCESS

The present invention relates to a process for the recovery of olefins from cracked gases employing a chemical absorption process. More particularly, the present invention relates to a process for improving the hydrogenation of acetylenes and dienes in the front end of an olefin recovery process.

BACKGROUND OF THE INVENTION

The processes for converting hydrocarbons at high temperatures, such as for example, steam-cracking, catalytic cracking or deep catalytic cracking to produce relatively high yields of unsaturated hydrocarbons, such as, for example, ethylene, propylene, and the butenes, are well known in the art. See, for example, Hallee et al., U.S. Pat. No. 3,407,789; Woebcke, U.S. Pat. No. 3,820,955; DiNicolantonio, U.S. Pat. No. 4,499,055; Gartside et al., U.S. Pat. No. 4,814,067; Cormier, Jr. et al., U.S. Pat. No. 4,828,679; Rabo et al., U.S. Pat. No. 3,647,682; Rosinski et al., U.S. Pat. No. 3,758,403; Li et al., U.S. Pat. No. 4,980,053; and Yongqing et al., U.S. Pat. No. 5,326,465.

It is also well known in the art that these mono-olefinic compounds are extremely useful in the formation of a wide variety of petrochemicals. For example, these compounds can be used in the formation of polyethylene, polypropylenes, polyisobutylene and other polymers, alcohols, vinyl chloride monomer, acrylonitrile, methyl tertiary butyl ether and other petrochemicals, and a variety of rubbers such as butyl rubber.

Besides the mono-olefins contained in the cracked gases, the gases typically contain a large amount of other components such as diolefins, hydrogen, carbon monoxide and paraffins. It is highly desirable to separate the mono-olefins into relatively high purity streams of the individual mono-olefinic components in order to facilitate downstream processing. To this end a number of processes have been developed to make the necessary separations to achieve the high purity mono-olefinic components.

An especially significant process for recovering olefins from cracked gases is a selective chemical absorption process described in Barchas et al., U.S. Pat. No. 5,859,304. In the Barchas et al. '304 patent, there is suggested the desirability for removing at least substantially all acetylenes and dienes from the depropanized cracked gas prior to the chemical absorption of the olefins. Removal of these acetylene and diene contaminants is beneficial because the acetylene and methyl acetylene will react with the absorbent solution to form potentially hazardous acetylides, and propadiene will be absorbed along with the olefins by the chemical absorbent thereby eventually contaminating the propylene product.

In Barchas et al. '304, a "deep" front end selective hydrogenation process is taught to effectuate the removal of at least substantially all of the acetylenes and dienes from the depropanized cracked gas prior to demethanization. The deep front end selective hydrogenation process disclosed in Barchas et al. '304 operates in the vapor phase and uses multiple catalysts beds, typically three with cooling between the beds. However, due to the severe conditions required in the last bed to hydrogenate the last traces of propadiene, it has been found that the process concomitantly hydrogenates some of the ethylene into ethane, typically around about 3%. The hydrogenation of ethylene into ethane increases the ethane recycle to the cracking furnaces, which results in increased feedstock consumption, larger equipment and increased processing costs. There is also a potential for the olefins to react uncontrollably with the large excess of hydrogen present in the cracked gas (a so-called runaway reaction). Additionally, the deep hydrogenation process of Barchas et al. '304 also has the disadvantage of running at relatively low space velocities (i.e., high gas residence times corresponding to larger catalyst volumes) in order to achieve the deep hydrogenation required.

Therefore, although the Barchas et al. '304 process has proved very beneficial to the art of recovering olefins from cracked gases, it would be highly desirable to provide an improved deep selective hydrogenation process which overcomes the aforementioned drawbacks.

SUMMARY OF THE INVENTION

It is therefore an object of the present invention to provide an improved process for the recovery of olefins from a cracked gas stream which is sufficient to produce the olefins at high purity levels, i.e., polymer grade.

It is a further object of the present invention to provide an improved hydrogenation process which can be employed with a chemical absorption process for recovering olefins from cracked gases.

It is another object of the present invention to provide a hydrogenation process with reduced feed consumption, smaller equipment, lower processing costs, reduced potential for runaway reactions, and/or lower catalyst cost.

To this end, the present invention provides an improved process for hydrogenating the acetylenes and dienes in a cracked gas stream by employing an upstream less severe initial partial hydrogenation process, followed by bulk removal of hydrogen, and a downstream polishing/scavenging process to hydrogenate the residual acetylenes and dienes and scavenge the residual hydrogen.

DETAILED DESCRIPTION OF THE PRESENT INVENTION

Figure 1:
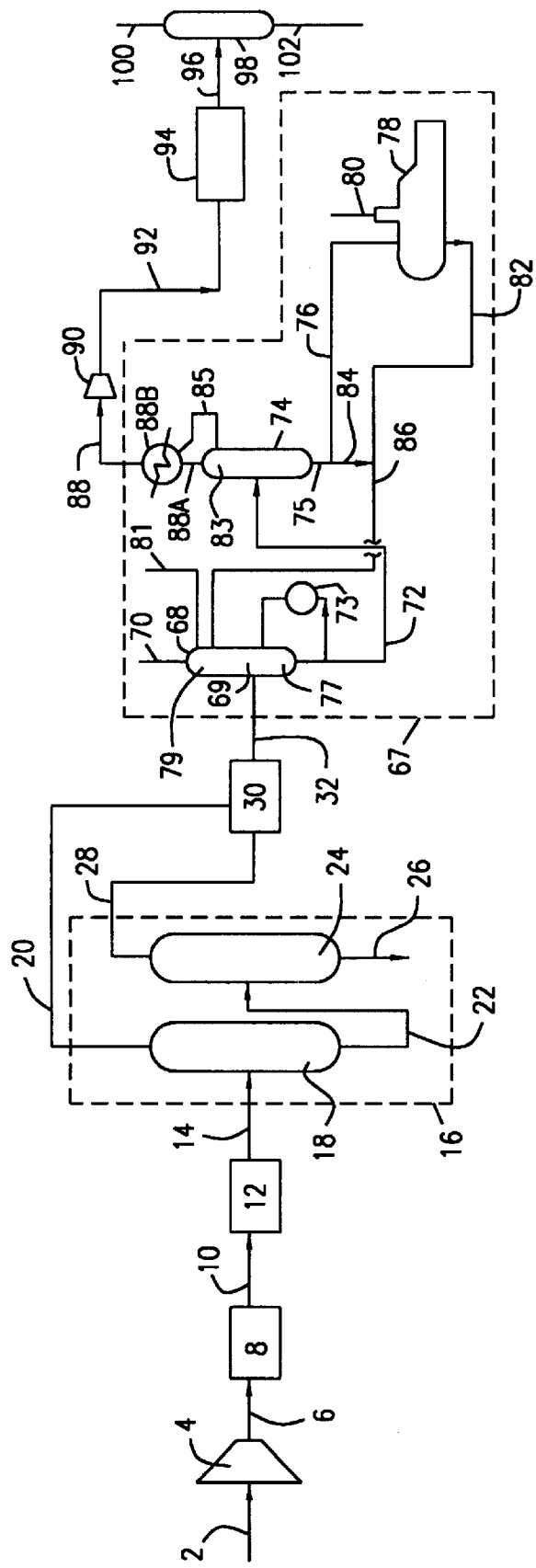
FIG. 1 depicts in flow chart manner an overall embodiment of the process of the present invention.

The present invention provides a novel deep selective hydrogenation process for hydrogenating a cracked gas stream comprising hydrogen, methane, ethane, ethylene, acetylene, propane, propylene, propadiene and methyl acetylene, the process comprising the steps of (a) partially hydrogenating the cracked gas stream to hydrogenate essentially all of the acetylenes and reducing the propadiene content to less than about 500 ppmv to produce a partially hydrogenated gas stream; (b) partially demethanizing the partially hydrogenated gas stream to remove at least about 80% of the methane and reduce the hydrogen concentration to less than about 5000 ppmv to produce a partially demethanized stream; and (c) further hydrogenating said partially demethanized stream to hydrogenate essentially all of the propadiene contained in said partially demethanized stream.

The present invention also provides a novel process for the recovery of olefins from cracked gases comprising the steps of (a) partially hydrogenating a cracked gas stream to hydrogenate essentially all of the acetylenes and reduce the propadiene content to less than about 500 ppmv to produce a partially hydrogenated gas stream; (b) partially demethanizing the partially hydrogenated gas stream to remove at least about 80% of the methane and reduce the hydrogen concentration to less than about 5000 ppmv to produce a partially demethanized stream; (c) further hydrogenating the partially demethanized stream to hydrogenate essentially all of the propadiene contained in the partially demethanized stream to produce a fully hydrogenated stream and reacting essentially all of the residual hydrogen with olefins; (d) contacting the fully hydrogenated stream with a metallic solution capable of selectively chemically absorbing the ethylene and propylene to produce a paraffin-rich gaseous stream and a chemically absorbed olefin-rich stream; and (e) recovering the olefins from the metallic chemical absorbent solution.

The gas streams useful as feedstocks in the process of the present invention can typically be any gas stream which contains light olefins, namely ethylene and/or propylene, in combination with other gases, particularly, hydrogen, acetylenes, dienes and saturated hydrocarbons. Typically, cracked gas streams for use in accordance with the practice of the present invention will comprise a mixture of butane, butenes, propane, propylene, ethane, ethylene, acetylene, methyl acetylene, propadiene, methane, hydrogen, and carbon monoxide.

The deep selective hydrogenation process of the present invention is, as mentioned hereinabove, especially useful in the practice of the process described in the Barchas '304 patent, which is incorporated in full herein by reference. In such an exemplary process, the cracked gas stream is preferably first compressed to a pressure ranging from about 100 psig to about 450 psig, preferably from about 250 psig to about 400 psig, in the compressing step to produce a compressed cracked gas stream. The compression may be effected in any compressor or compression system known to those skilled in the art. The compressed gas is then caustic washed to remove carbon dioxide and other acid gases, as is well known to those skilled in the art. Any of the caustic washing processes known to those skilled in the art may be employed in the practice of the present invention. The washed and compressed gas is then dried, such as over a water-absorbing molecular sieve to a dew point of from about −150° F. to about −200° F. to produce a dried stream. The drying serves to remove water before downstream chilling of the process stream.

The dried process stream is then preferably depropanized to recover butadiene and prevent heavier components from condensing in downstream equipment or fouling the front-end hydrogenation system. The depropanizer typically operates at pressures ranging from about 50 psia to about 300 psia and is normally equipped with a reboiler. Optionally, a dual depropanizer system may be employed, the first depropanizer operating at relatively high pressures, such as from about 150 to about 300 psia, and the second depropanizer operating at pressures ranging from about 50 to about 125 psia.

The bottoms from the depropanizer comprises substantially all of the $C_4+$ hydrocarbons including the butadiene which enhances the value of this stream. This stream may be separated into its component parts for butene recovery, butadiene recovery, pentene recovery, and recycling of the butanes and pentanes to the cracking reaction zone, such as a steam cracker, as desired. The embodiment of an upstream depropanizer system also eliminates the need for a gasoline decanting and wash system in the downstream absorption system.

The overhead from the depropanizer comprises substantially all of the $C_3$ and lighter hydrocarbons. This overhead stream is processed in accordance with the deep selective hydrogenation method of the present invention to remove at least substantially all of the acetylenes and dienes contained therein, i.e., down to ppm levels. The presence of these compounds can adversely affect the stripping solution in the downstream absorption system. Thus, substantial, or essentially complete, removal of these compounds is preferable.

The hydrogenation system of the present invention comprises a partial hydrogenation system, a partial demethanization system and a finishing hydrogenation system. In the partial hydrogenation system essentially all of the acetylenes are hydrogenated and the propadiene is hydrogenated down to levels of less than about 500 ppmv, preferably less than about 300 ppmv, to produce a partially hydrogenated gas stream. The partial hydrogenation system may employ any of the catalysts well known to selectively hydrogenate acetylene, methyl acetylene and propadiene. The Group VIII metal hydrogenation catalysts are the most commonly used and are preferred. Examples of suitable catalysts are more fully disclosed in the literature. See for example, La Hue et al., U.S. Pat. No. 3,679,762; Cosyns et al., U.S. Pat. No. 4,571,442; Cosyns et al., U.S. Pat. No. 4,347,392; Montgomery, U.S. Pat. No. 4,128,595; Cosyns et al., U.S. Pat. No. 5,059,732 and Liu et al., U.S. Pat. No. 4,762,956.

The conditions employed in the first partial hydrogenation reactor according to the present invention are sufficient to hydrogenate essentially all of the acetylenes and the bulk of the propadiene. Typically two series reactors are generally required to achieve the partial upstream hydrogenation of the present invention. Generally, the selective hydrogenation process will be carried out over a temperature range of from about 50° C. to about 100° C., a pressure range of from about 200 psia to about 400 psia, and space velocities ranging from about 3000 $hr^{-1}$ to about 10,000 $hr^{-1}$. Excess hydrogen, above the stoichiometric requirements for the selective hydrogenation reactions, is contained in the feed to the partial hydrogenation reactor(s). The process can be carried out employing the catalyst in a fixed bed or other type of contacting means known to those skilled in the art.

The effluent from the first partial hydrogenation reactor is directed to a partial demethanization system in which the partially hydrogenated gas stream is demethanized to remove at least about 80% of the methane and reduce the hydrogen concentration to less than about 5000 ppmv to produce a partially demethanized stream. The partial demethanization requirements of the present invention are generally less stringent that those described in U.S. Pat. No. 5,859,304 where about the same amount of methane but essentially all of the hydrogen is removed. The less stringent hydrogen removal requirement of the present invention results in a simpler and less expensive partial demethanizer design and reduced refrigeration requirements.

The partial demethanization overhead comprises substantially methane and hydrogen. Thus, the bottoms stream from the partial demethanizer has a substantially increased concentration of propadiene, on the order of several hundred ppmv, due to the removal of methane and hydrogen, although the actual amount of propadiene contained in the bottoms has not changed from the feed to the partial demethanizer. The removal of a large portion of hydrogen in the demethanizer overhead reduces the concentration of hydrogen in the bottoms stream to preferably from about 1000 ppmv to about 5000 ppmv.

Because the concentration of hydrogen is low in the demethanizer bottoms as compared with the amount of hydrogen in the feed to the initial hydrogenation reactor(s), the demethanizer bottoms can be fed to a subsequent finishing hydrogenation system to hydrogenate essentially all of the propadiene contained in said partially demethanized stream. Due to the relatively low concentration of hydrogen in the demethanizer bottoms stream which is fed to the finishing hydrogenation system, the reactor temperature can be increased without concern of a runaway reaction, thereby further enabling substantially complete hydrogenation of propadiene.

Additionally, the finishing hydrogenation system acts to remove a portion of the remaining hydrogen contained in the process stream by reaction with the propadiene in the finishing hydrogenation reaction. The balance of the remaining hydrogen reacts with olefins. Olefin hydrogenation in the finishing hydrogenation system is also reduced because the amount of excess hydrogen contained in the stream is lower. Typical olefin losses in accordance with the practice of the process of the present invention are on the order of about 1% and less.

In a preferred finishing hydrogenation system a dual bed reactor is employed. In the first bed the hydrogenation of the propadiene is completed and in the second bed olefin hydrogenation to scavenge the remaining hydrogen is effected. Preferably, the hydrogen content of the process stream leaving the finishing hydrogenation system is less than about 50 ppmv, more preferably less than 10 ppmv and most preferably there is essentially no hydrogen remaining, i.e., less than about 1 ppmv.

The typical conditions employed in the finishing hydrogenation reactor system according to the present invention are sufficient to hydrogenate essentially all of the propadiene. Typically one reactor is required to achieve essentially complete propadiene hydrogenation and hydrogen removal. The finishing hydrogenation can employ any of the hydrogenation catalysts known to those skilled in the art for hydrogenating propadiene, such as those described hereinabove.

Generally, the finishing hydrogenation process will be carried out over a temperature range of from about 50° C. to about 70° C., a pressure range of from about 200 psia to about 400 psia, and space velocities ranging from about 2000 $hr^{-1}$ to about 10,000 $hr^{-1}$. The required hydrogen for completing the propadiene hydrogenation is contained in the feed to the finishing hydrogenation reactor. The process can be carried out employing the catalyst in a fixed bed or other type of contacting means known to those skilled in the art.

Thus, the present invention provides further significant advantages in lower ethane recycle, lower feed consumption, smaller equipment and lower processing costs. Further, there is less risk of a runaway reaction.

It is recognized that depending on the feed stream being processed in accordance with the process of the present invention, the amount of methane contained in the partial demethanizer bottoms stream may be uneconomically high when producing a bottoms stream containing 1000–5000 ppmv of hydrogen. In these cases, it is contemplated by the present invention to employ an alternative partial demethanizer which is designed to produce a lower hydrogen content stream, from about 1000 ppmv down to about 1 ppmv hydrogen. Additional hydrogen can then be added to the demethanizer bottoms stream prior to the finishing hydrogenation reactor to provide sufficient hydrogen to effect the propadiene hydrogenation. The additional hydrogen can be supplied from an outside hydrogen stream, or can be a low purity hydrogen stream which may conveniently be comprised of a portion of the partial demethanizer overhead.

The effluent from the finishing hydrogenation reactor system containing mostly the $C_{2-3}$ hydrocarbon components with some methane and essentially no hydrogen, acetylenes or dienes, are then passed to the selective chemical absorption system of the present invention.

In the absorption section, the $C_2/C_3$ vapor stream from the demethanizer system is scrubbed in an absorption tower with a scrubbing solution to separate the paraffins from the olefins. The olefins and any residual diolefins are chemically complexed with the scrubbing solution and are removed from the paraffinic components. The scrubbed gases, mainly paraffins and any residual hydrogen, are removed from the top of the absorber. The olefins complexed with the scrubbing solution are removed from the bottom of the absorber.

The absorption tower may have any suitable number of theoretical stages, depending upon the composition of the gaseous mixture to be treated, the purity required for the ethylene and propylene and the type of complexing solution employed. The absorber preferably operates with the pressure typically at about 100 psig and the temperature maintained as low as practical without the need for refrigeration, for example from about 25 to about 35° C.

The scrubbing solution may contain an aqueous solution of any of a number of certain heavy metal ions which are known to form chemical complexes with olefins, e.g., copper(I), silver(I), platinum(II) and palladium(II). Especially useful in the practice of the present invention is a solution of a silver[+1] salt. The silver[+1] salts which are generally useful include, but are not limited to, silver[+1] acetate, silver[+1] nitrate and silver[+1] fluoride, and mixtures of any of the foregoing. Preferred for use in the present invention is silver[+1] nitrate.

Where copper is employed as the metallic salt, it is preferably employed in solution form buffered with a soluble organic nitrogen ligand, such as pyridine, piperidine, hydroxypropionitrile, diethylene triamine, acetonitrile, formamide and acetamide, derivatives thereof and mixtures of any of the foregoing. See, generally, Davis et al., EP 0 699 468. Especially preferred is pyridine and/or hydroxypropionitrile.

The concentration of silver[+1] salt in the aqueous scrubbing solution is at least about 0.5 moles of salt per liter of solvent, and preferably at least about 2 moles of salt per liter of solvent.

The absorbers of the present invention may further comprise a water wash section in the upper portion of the absorber and a prestripping zone in the lower section of the absorber. In the water wash section, water is added to the top of the absorber tower to reduce entrainment of the scrubbing solution.

In the prestripper section, at least a portion of the scrubbing solution containing the metallic salt:olefin complex is fed to a reboiler for heating to a temperature of from about 40° C. to about 60° C., preferably from about 45° C. to about 55° C. to desorb at least a substantial portion of any physically absorbed paraffins. Inexpensive quench water may be conveniently used as the heating medium as well as any other heating means known to those of ordinary skill in the art.

The bottoms of the absorber containing the metal salt:olefin complex are removed from the absorber for scrubbing solution recovery and olefin component purification. In the first step of the further processing, the bottoms stream is fed to an olefin stripper for separation into an olefin rich gas stream and a spent scrubbing liquid stream.

In the olefin stripper, the desorption is effected, preferably in a packed tower or flash drum, by dissociating the olefins from the metal salt complexes using a combination of increased temperature and lower pressure. At temperatures ranging from about 65° C. to about 110° C., preferably from about 70° C. to about 85° C., and pressures ranging from about 5 psig to about 50 psig, the ethylene and propylene readily dissociate from the metal salt complexes. Inexpensive quench water can conveniently be used as the heating medium for providing olefin stripper temperatures in the lower end of the range, as well as any other heating means known to those of ordinary skill in the art. The olefin stripper is preferably equipped with a water wash section in the top of the stripper to prevent entrainment of the scrubbing solution with the desorbed gases.

It is understood that the olefin stripper or flash drum can comprise multi-stage stripping or flashing for increased energy efficiency. In such systems, the rich solution is flashed and stripped at progressively higher temperatures and/or lower pressures. The design of such systems is well known to those skilled in the art.

The stripped scrubbing solution is removed from the olefin stripper for reclaiming and recycling. All or a portion of the stripped solution may be passed via a slip stream to a reclaimer to decompose any acetylides which may have formed from non-hydrogenated acetylene and methyl acetylene.

Where a metal salt/ligand complex is employed in the chemical absorbing solution, a ligand recovery system may be employed as described in commonly assigned, copending U.S. patent application Ser. No. 08/696,578.

The stripped olefins from the olefin stripper are then compressed to about a pressure ranging from about 250 psig to about 350 psig, preferably about 300 psig. A two stage centrifugal compressor is typically suitable for this compression, although other means known to those skilled in the art may be employed. The compressed olefins are then dried.

The dried mixed olefins are preferably then fed to a deethylenizer tower which operates at a pressure ranging from about 250 psig to about 300 psig, generally about 275 psig. Typically, low level propylene refrigeration is sufficient for feed chilling and to condense the overheads in the deethylenizer. Quench water or other suitable means may be employed for reboiling. Polymer-grade ethylene is taken at or near the top of the deethylenizer. A small vent containing residual methane and hydrogen may also be taken off the top of the tower or reflux drum, if necessary. Polymer grade propylene is removed at or near the bottom of the deethylenizer.

DESCRIPTION OF THE PREFERRED EMBODIMENTS

Referring to FIG. 1, a mixed gaseous hydrocarbon stream, such as a cracked gas stream, in a line 2 is fed to a compressor 4 which operates to compress the gas stream to a pressure of about 300 psig. The compressed gaseous stream in a line 6 is caustic washed in caustic washer 8 and fed to a drier 12 via a line 10. The dried gas stream in a line 14 is then fed to a depropanizer system 16.

In the depropanizer system 16 the dried gas stream 14 enters a first high pressure depropanizer 18 operating at a pressure of about 250 psig to produce a first $C_3$ and lighter hydrocarbon overhead stream in a line 20 and a first $C_4$ and heavier bottoms stream in a line 22. The first depropanizer bottoms in a line 22 is then fed to a low pressure depropanizer 24 operating at a pressure of about 100 psig to separate the residual $C_3$ and lighter hydrocarbons in an overhead line 28 from the $C_4$ and heavier hydrocarbons in a bottoms line 26. The $C_4$ and heavier hydrocarbons bottoms from the second depropanizer in a line 26 may then be further processed as desired (not shown).

The $C_3$ and lighter hydrocarbon overhead stream from the first depropanizer in a line 20 and the residual $C_3$ and lighter hydrocarbon overhead stream from the second depropanizer in a line 28, leave the depropanizer system 16 and are fed to the improved deep selective hydrogenation system 30 of the present invention. A first embodiment of the deep selective hydrogenation system of the present invention is shown in FIG. 2.

Figure 2:
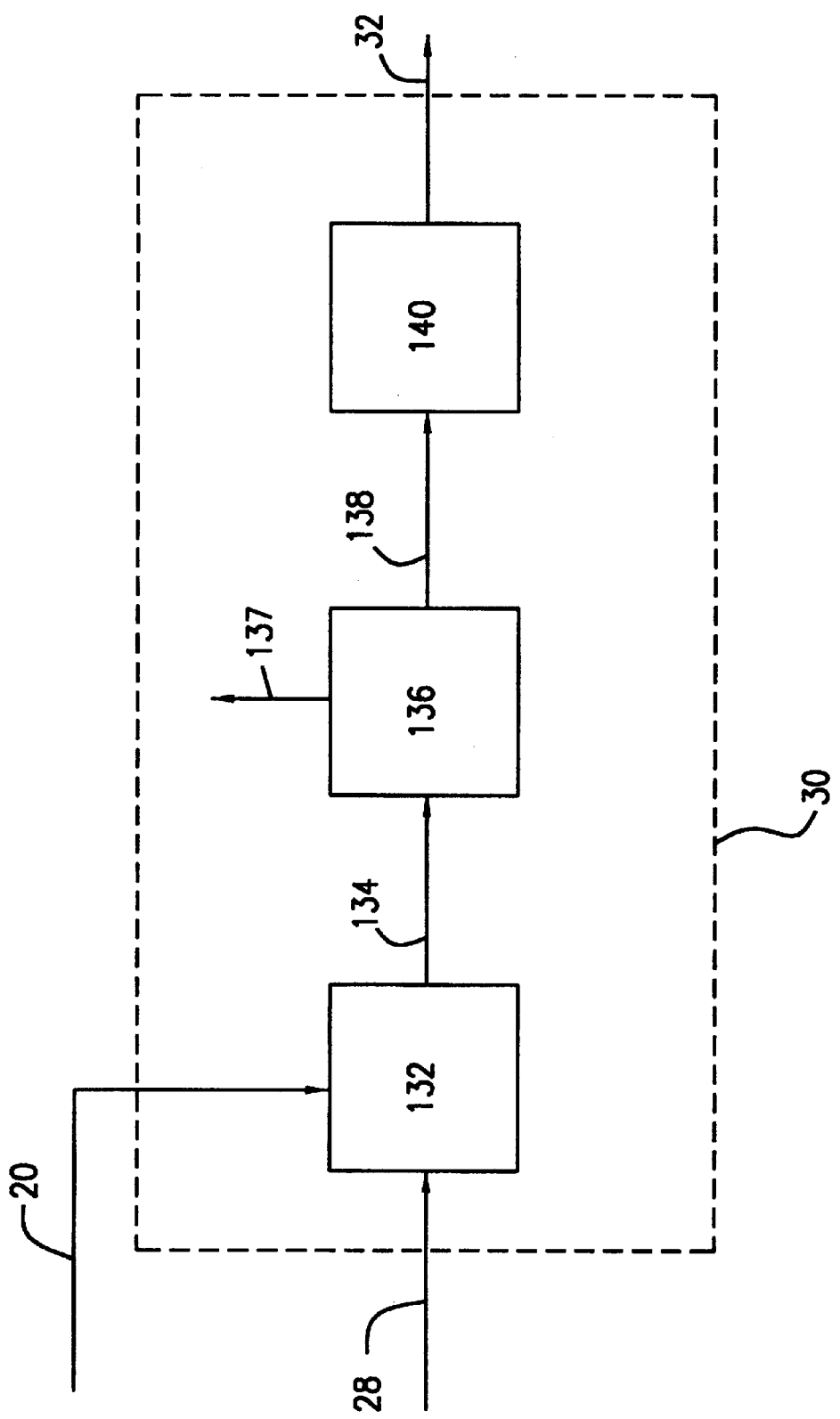
FIG. 2 depicts in flow chart manner an embodiment of a deep selective hydrogenation process of the present invention.

Referring to FIG. 2, the compressed, depropanized, caustic washed and dried gas streams in lines 20 and 28 are fed to a first hydrogenation reactor system 132 in deep selective hydrogenation system 30. In the first hydrogenation reactor system 132, preferably two serially connected reactors, substantially all of the acetylene and methyl acetylene are hydrogenated to the corresponding olefin, and a substantial portion of the propadiene is also hydrogenated, i.e., to a concentration of less than about 1000 ppmv, preferably less than about 500 ppmv, and more preferably from about 200 to about 300 ppmv. The partially hydrogenated stream exits the initial hydrogenation reactor system 132 in a line 134 and is fed to a partial demethanization zone 136.

In the partial demethanization zone, the partially hydrogenated stream is distilled to reduce the concentration of hydrogen contained in the partially hydrogenated stream to less than about 5000 ppmv, preferably from about 1000 ppmv to about 5000 ppmv in the demethanizer bottoms stream. Typically, in such a demethanization process, from about 80 to about 90% of the methane is also removed in the overhead stream along with the hydrogen. Any known demethanization scheme may be employed in accordance with the present invention in order to partially demethanize the partially hydrogenated stream.

The overhead from the demethanization zone 136 containing predominantly methane and hydrogen is removed in a line 137. The demethanizer bottoms containing the partially demethanized process stream is removed in a line 138 and fed to the finishing hydrogenation reactor zone 140. In the finishing hydrogenation reactor zone 140 the residual propadiene is hydrogenated with the hydrogen in the process stream. The hydrogenated process stream having an acetylene and diene concentration below about 50 ppmv, preferably below about 10 ppmv, is removed via a line 32 for further processing as described hereinbelow.

Preferably finishing hydrogenation reactor zone 140 comprises a dual bed reactor. In the first bed, the propadiene hydrogenation is finished by hydrogenating the propadiene concentration down to below about 50 ppmv, preferably below about 20 ppmv. In the second bed, hydrogen scavenging is effected by reacting remaining hydrogen with olefins to reduce the hydrogen concentration to less than about 50 ppmv, preferably less than about 10 ppmv, and more preferably less than about 1 ppmv.

Figure 3:
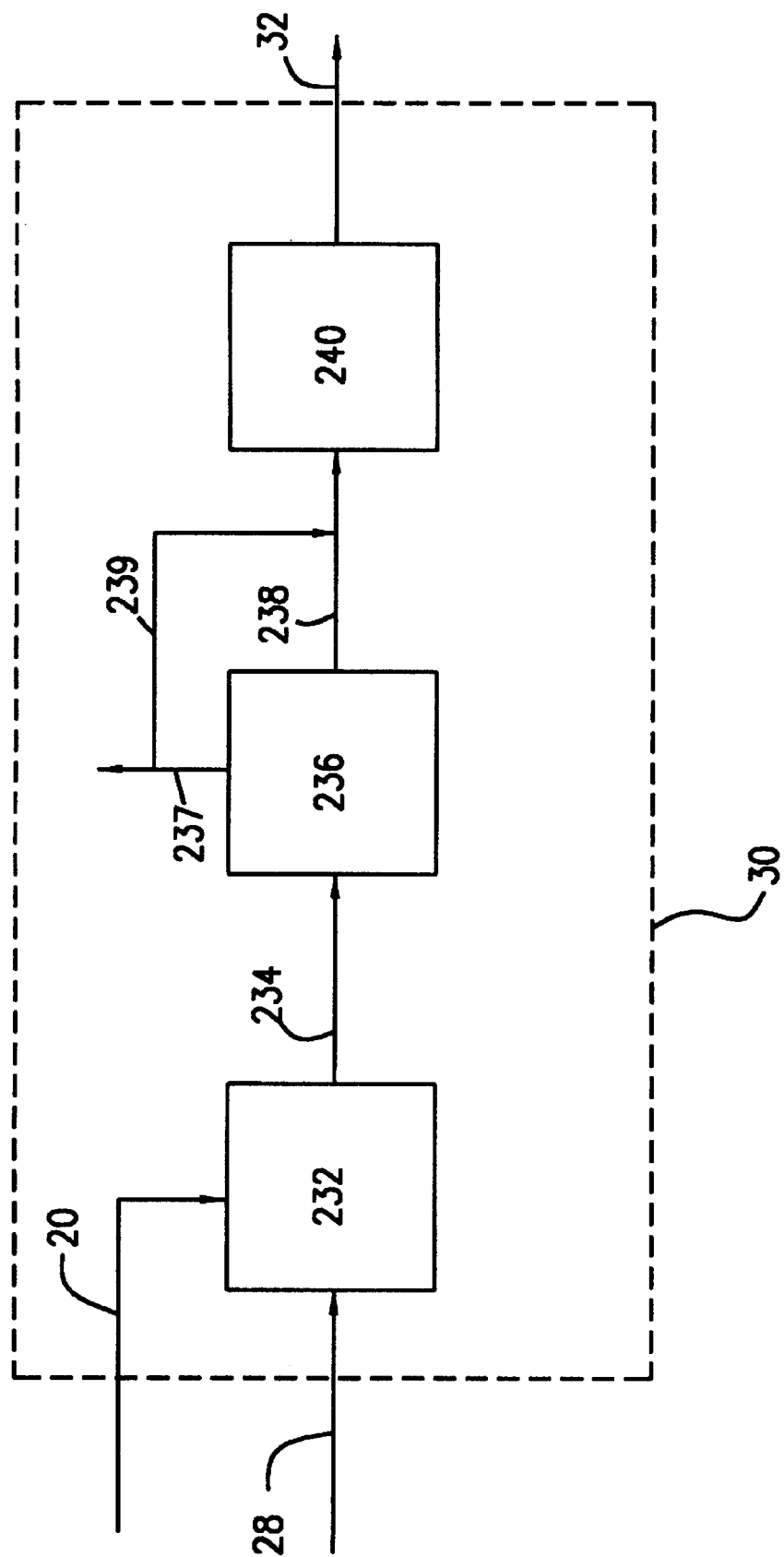
FIG. 3 depicts in flow chart manner an alternative embodiment of the deep selective hydrogenation process of the present invention.

Alternatively, referring to FIG. 3, a more severe partial demethanization is employed where the amount of hydrogen in the bottoms from the demethanizer is insufficient for the finishing hydrogenation zone. In this scheme, the compressed, depropanized, caustic washed and dried gas stream in lines 20 and 28 are fed to a first hydrogenation reactor system 232 in deep selective hydrogenation system 30. In the first hydrogenation reactor system 232, preferably two serially connected reactors, substantially all of the acetylene and methyl acetylene are hydrogenated to the corresponding olefin, and a substantial portion of the propadiene is also hydrogenated, i.e. to a concentration of less than about 1000 ppmv, preferably less than about 500 ppmv, more preferably from about 200 to about 350 ppmv. The partially hydrogenated stream exits the initial hydrogenation reactor system 232 in a line 234 and is fed to a partial demethanization 236. In partial demethanization zone 236, the partially hydrogenated stream is demethanized to produce a demethanized bottom stream 238 having less than 1000 ppmv of hydrogen, down to about 1 ppmv hydrogen. Accordingly, the overhead from the demethanization zone 236 in a line 237 is a hydrogen containing stream which also comprises substantial amounts of methane.

In order to provide sufficient hydrogen to complete the hydrogenation of the propadiene in downstream finishing hydrogenation reactor zone 240, makeup hydrogen is added to the partially demethanized bottoms streams 238. This make up hydrogen may be obtained from any source, but conveniently, may be obtained directly from the demethanizer overhead stream 237 as a side stream 239. The amount of makeup hydrogen can be determined from the stoichiometric amount of propadiene and residual acetylenes needed to be hydrogenated in finishing reactor zone 240 and is generally in at least 100% excess. The hydrogenated stream exits the finishing reaction zone 240 in a line 32 for further downstream processing as described hereinbelow.

Figure 4:
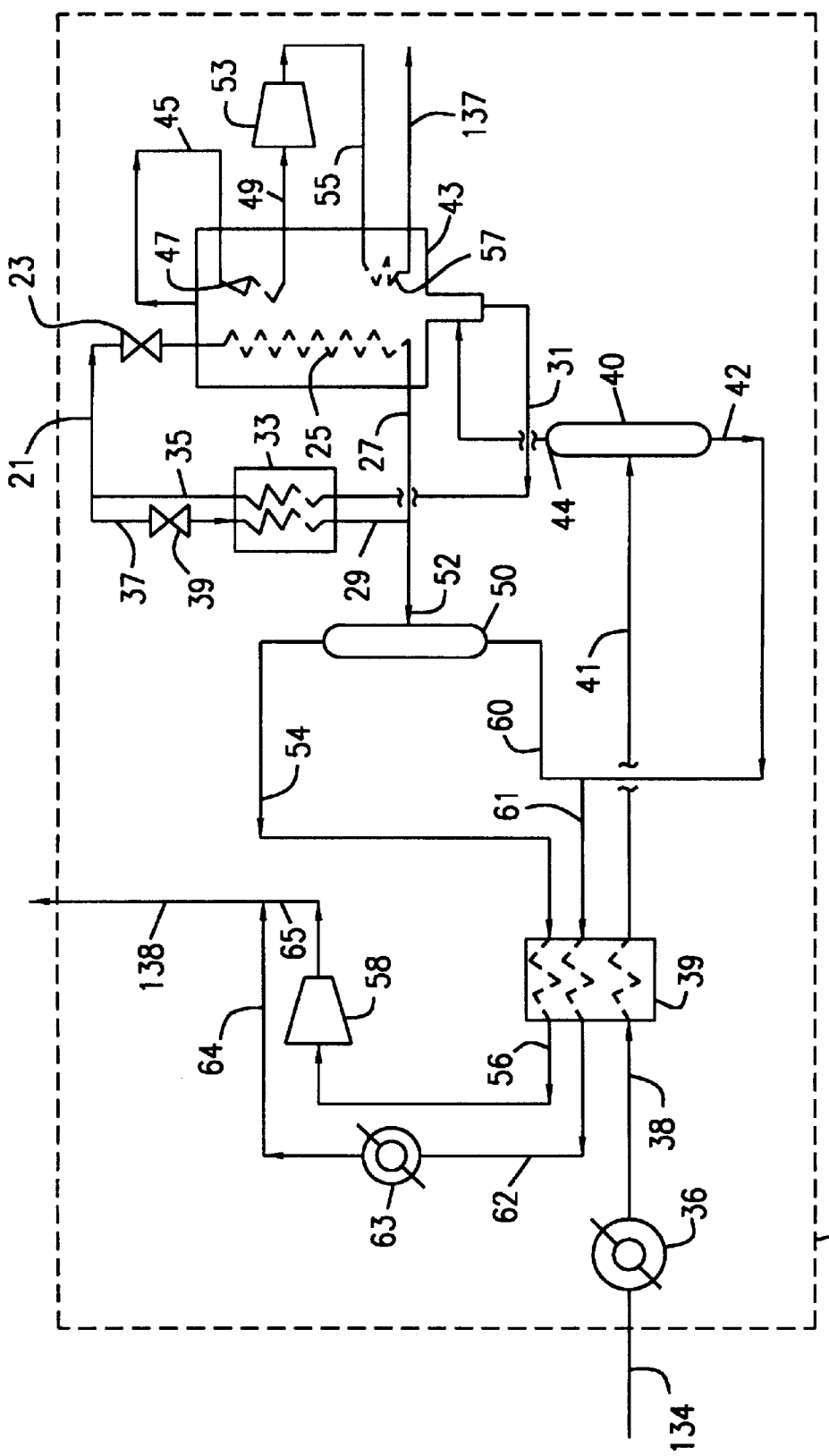
FIG. 4 depicts in flow chart form an embodiment of a partial demethanization process useful in the practice of the present invention.

A preferred demethanization system which may be employed as demethanization system 136 (or 236) is shown in FIG. 4. Referring to FIG. 4, the partially hydrogenated stream exiting the initial hydrogenation reactor system in a line 134 is fed to a partial demethanization zone 136. In the partial demethanizer zone 136 the process stream 134 is chilled and partially condensed in a chiller 36 to a temperature ranging from about –30° C. to about –40° C., preferably to about –35° C., using propylene refrigeration. The chilled effluent in a line 38 is then further chilled to about –45° C. and partially condensed in exchanger 39. The chilled stream in a line 41 is then fed to a separator 40 for separation into an overhead gaseous stream comprising a portion of the hydrogen, a portion of the methane and a minor portion of the $C_{2-3}$ hydrocarbons in a line 44. The liquid condensate comprising a portion of the $C_{2-3}$ hydrocarbons and a minor portion of the methane and the hydrogen is removed via a bottoms line 42.

The overhead line 44 is then fed to a demethanizer tower or refluxed exchanger 43, where at least a major portion of the methane (at least about 80%, such as from about 80% to about 90%) and the desired amount hydrogen are removed from the top of the refluxed exchanger 43 via a line 45. The desired amount of hydrogen to be removed can be determined by the downstream stoichiometric requirements of the propadiene hydrogenation in the finishing hydrogenation reactor. The gaseous stream in line 45 is at a temperature of about –115° C. and provides refrigeration to exchanger 47 of refluxed exchanger 43. The gaseous stream exits the exchanger 47 as a warmed gaseous stream in a line 49 at a temperature of about –100° C. The warmed gaseous stream in a line 49 is then expanded to a temperature of about –145° C. in expander 53 and warmed again as a line 55 in exchanger 57 of refluxed exchanger 43 to a temperature of about –60° C. The warmed stream leaving exchanger 57 in a line 137 can be recovered, or optional, additional refrigeration can be recovered from this stream before sending it to the fuel gas header (not shown). In the embodiment of FIG. 3, a portion of this stream 237 can be used as a low purity hydrogen make up stream 239 as described hereinabove.

The liquid bottoms from the refluxed exchanger 43 comprising mostly $C_{2-3}$ hydrocarbons and some methane and hydrogen are removed via a line 31 and cooled in exchanger 33. The stream leaves exchanger 33 in a line 35 and is split into two streams. One of the split streams in a line 37 is flashed across a valve 39 and partially vaporized in exchanger 33 and exits in a line 29. The other stream in a line 21 is flashed across a valve 23 and partially vaporized in exchanger 25 of refluxed exchanger 43 and exits in a line 27. The two partially vaporized streams in lines 27 and 29 are combined into a line 52 and fed to a separator 50. The overhead exits the separator 50 in a line 54 at a temperature of about –70° C. The overhead is then warmed to a temperature of about –40° C. in exchanger 39 and leaves exchanger 39 line 56. The warmed vapor in a line 56 is then compressed in a compressor 58.

The liquid from separator 50 in a line 60 is combined with the liquid in a line 42 to form a line 61 for partial vaporization in exchanger 39. The mixture leaving the exchanger 39 in a line 62 is then totally vaporized in vaporizer 63 by condensing propylene refrigerant. The vapor leaving the vaporizer 63 in a line 64 is combined with the compressed vapor in a line 65 to form a combined vapor stream in a line 138 comprising essentially all of the $C_{2-3}$ hydrocarbons, some methane and less than about 5000 ppmv of hydrogen, preferably from about 1000 to about 5000 ppmv of hydrogen. In the case of the partial demethanization system of FIG. 3, the hydrogen content of stream 238 is less than about 1000 ppmv, preferably from about 1 to about 1000 ppmv. This combined stream in a line 138 is then sent to the finishing hydrogenation reactor system 140 as discussed hereinabove.

Referring to FIG. 2, the process stream 138 exiting the partial demethanizer zone 136 is then hydrogenated in finishing hydrogenation zone 140. The finished hydrogenated stream containing essentially no acetylenes or dienes, i.e., less than about 50 ppmv each, preferably less than about 10 ppmv each, and also containing essentially no hydrogen, i.e., less than 50 ppmv, preferably less than about 10 ppmv, and more preferably less than about 1 ppmv, is removed from the finishing hydrogenation zone in a line 32 for feeding to the chemical absorption zone 67 as described hereinbelow.

Returning to FIG. 1, in the chemical absorption system 67, the $C_3$ and lighter hydrocarbon vapors in the line 32 are fed into a middle scrubbing section 69 of an absorber tower 68 operating at a pressure ranging from about 50 psig to about 200 psig, preferably at about 100 psig. In the scrubbing section 69 of absorber tower 68 the feed is scrubbed with a scrubbing solution which enters near the top of the tower 68 via line 86. The active metal complex, preferably silver nitrate, in the scrubbing solution chemically absorbs at least a substantial portion of the olefin components and is directed towards a bottom prestripping section 77 of the tower 68. The paraffin gases are not chemically absorbed by the active metal complex and rise to the top of the tower to a water wash section 79 where they are water washed with water entering via a line 81 to recover any entrained scrubbing solution. The paraffins and any residual hydrogen are removed out of the top of tower 68 via an offgas line 70. This absorber offgas stream may be conveniently recycled to the cracking furnace.

The scrubbing solution containing the chemically absorbed olefins proceeds downward through the tower 68 and enters a pre-stripping section 77 in the lower section of tower 68 which is preferably equipped with a reboiler 73 heated by quench water (not shown) for reboiling the scrubbing solution to desorb any physically absorbed paraffins. Alternatively, if the physically absorbed paraffins can be tolerated in the olefin products, the reboiler can be eliminated. The scrubbed liquid rich in ethylene and propylene and substantially free of paraffins is removed from the bottom of tower 68 via a stream 72.

The scrubbed liquid rich in olefins in a stream 72 is directed next to an olefin stripper 74 (or optionally a flash drum or series of flash drums) for desorption of the olefins from the spent scrubbing liquid using a combination of increased temperature and lower pressure as described hereinabove. The dissociated olefins are washed in an upper water wash section 83 of olefin stripper 74 which is supplied with water via a line 85 to recover any entrained spent scrubbing liquid. The stripped gas stream rich in olefins and substantially free of scrubbing liquid issuing from the olefins stripper 74 is removed via a line 88A and cooled in condenser 88B. Condensed water in a line 85 from condenser 88B is sent to the olefin stripper 74 as described hereinabove. The cooled stripped gas is removed via a line 88 for further processing into ethylene and propylene component rich product streams as described hereinbelow.

The lean scrubbing solution is removed from the bottom of the olefin stripper 74 via a line 75. At least a portion of the solution in a slipstream line 76 is preferably directed to a reclaimer 78 for decomposition of acetylides formed from residual acetylenes. The desorbed components exit the reclaimer via a vent line 80 and the reclaimed scrubbing solution is removed from the reclaimer 78 via a line 82.

The reclaimed scrubbing solution in a line 82 is merged with the other portion of the stripper bottoms in a line 84 to form a scrubbing solution recycle line 86 for recycling to the absorber tower 68.

The stripped gas stream rich in olefins issuing from the olefins stripper 74 in a line 88 is directed to an olefin compressor 90 for compression to a pressure ranging from about 200 psig to about 300 psig. The compressed olefin rich stream is removed from the compressor 90 in a line 92 for feeding to a dryer 94 operating at about 300 psig and about 40° C. The dried compressed olefin rich stream in a line 96 is then fed to a deethylenizer tower 98.

In the deethylenizer tower 98 which operates at from about 250 psig to about 300 psig, preferably about 275 psig, polymer grade ethylene is removed from a line near the top of the tower 98 as ethylene-rich product stream 100. Residual methane and hydrogen may optionally be removed via a vent line at the top of the tower or a reflux drum (not shown). Polymer grade propylene is then removed from the bottom of the tower 98 as polymer-grade product stream 102.

EXAMPLES

The following examples illustrate the present invention. They are not to be construed to limit the appended claims in any manner whatsoever.

TESTING APPARATUS

The apparatus employed in the examples was a bench-scale water jacketed downflow reactor tube having an inside diameter of about 19 millimeters with a single, fixed catalyst bed volume of 25 cubic centimeters. The water circulation was a closed loop system utilizing a controlled temperature recirculator to cool the reactor and preheat the hydrocarbon feed mixture to provide approximately isothermal reaction conditions. The top and bottom of the catalyst bed were fitted with a thermocouple.

FEEDSTOCK

The feedstock to the reactor was prepared from individual component cylinders of carbon monoxide, hydrogen, methane, acetylene, ethylene, propylene and MAPD (methyl acetylene/propadiene). The components were blended to approximate a typical depropanized cracked gas feedstock composition.

Comparative Examples 1 and 2

The catalyst employed in these examples was a commercially available hydrogenation catalyst sold under the trade name G-83A by United Catalyst Incorporated (UCI). G-83A is a palladium based catalyst with no promoters added. In Comparative Examples 1 and 2, 3/16 inch extruded tables of catalyst G-83A were employed. In Comparative Example 1, all three series reactors employed a nominal catalyst space velocity of 5000 GHSV. In Comparative Example 2, the first two reactors employed a nominal catalyst space velocity of 5000 GHSV and the third reactor employed a nominal catalyst space velocity of 2500 GHSV. The results are set forth in Table 1 below.

TABLE 1

| Reactor | 1A | 1B | 1C | 2C |
|---|---|---|---|---|
| Feedstock, mol basis | A | B | C | C |
| Catalyst | X | X | X | X |
| GHSV | 5000 | 5000 | 5000 | 2500 |
| Reactor Inlet Temp. ° F. | 147 | 160 | 165 | 174 |
| Reactor pressure, psig | 308 | 300 | 310 | 304 |
| C2H2 out, ppm | ND | ND | ND | ND |
| MA out, ppm | 167 | 7 | ND | ND |
| PD out, ppm | 502 | 134 | 48 | 16 |
| C2H4 gain (mol %) | (0.15) | (1.1) | (1.0) | (6.5) |
| C3H6 gain (mol %) | 0.49 | 0.14 | 0.03 | 0.13 |

A = 16.0% H2, 443 ppm CO, 28.9% CH4, 511 ppm C2H6, 45.0% C2H4, 255 ppm C3H8, 8.9% C3H6, 0.13% PD, 0.48% C2H2, 0.43% MA
B = 11.9% H2, 407 ppm CO, 31.7% CH4, 79 ppm C2H6, 46.3% C2H4, 298 ppm C3H8, 9.9% C3H6, 422 ppm PD, 1450 ppm MA
C = 13.3% H2, 669 ppm CO, 21.5% CH4, 69 ppm C2H6, 54.0% C2H4, 361 ppm C3H8, 11.1% C3H6, 103 ppm PD, 294 ppm MA
ND = Not detected
X = G-83A catalyst, 3/16" Tablets From Table 1 it can be seen that a single bed of G-83A at a nominal catalyst space velocity was sufficient to eliminate the acetylene with a bed inlet temperature of 147° F. Also, while the second bed almost entirely eliminated the methyl acetylene, the loss of ethylene was more that 1 mol percentage point, or more than 2 percent on the 46.3 mol percent in the second stage feed. Methyl acetylene was eliminated in the third stage with a nominal 5000 GHSV, but propadiene was at a relatively high 48 ppm by mol, and an additional 1 mol percent of ethylene loss resulted.

In the second comparative example with a lower nominal space velocity, the propadiene conversion was higher with 16 ppm by mol remaining, but an additional 6.5 mol percent of ethylene was converted.

Example 3

Example 3 shows the improved results obtained in accordance with the present invention. In this example, the third reactor stage feed was mixed to approximate the stream from the bottom of a demethanizer after the cracked gas had been treated in the first two "front end" hydrogenation reactor system. The feed mixture was approximated based on a demethanizer running in a partial demethanizing mode allowing enough hydrogen to be left in the bottoms stream to support hydrogenation of the propadiene in the third "back end" reactor. In the third reactor a standard UCI vapor phase C3 treatment catalyst under the trade name G-55B was employed. The results are summarized in Table 2 below.

TABLE 2

| Reactor | 3A | 3B | 3C |
| --- | --- | --- | --- |
| Feedstock, mol basis | A | B | C |
| Catalyst | Y | Y | Z |
| GHSV | 5000 | 5000 | 5000 |
| Reactor Inlet Temp. ° F. | 133 | 135 | 124 |
| Reactor pressure, psig | 300 | 300 | 250 |
| C2H2 out, ppm | ND | ND | ND |
| MA out, ppm | 263 | ND | ND |
| PD out, ppm | 973 | 252 | 10 |
| C2H2 conversion, % | 100 | — | — |
| MA conversion, % | 95 | 100 | — |
| PD conversion, % | 71 | 65 | 98 |
| C2H4 gain, mol % | 0.25 | (0.38) | (0.26) |
| C3H6 gain, mol % | 0.73 | 0.28 | 0.21 |
| Total C2H4 gain, mol % | 0.25 | (0.13) | (0.39) |
| Total C3H6 gain, mol % | 0.73 | 1.01 | 1.21 |

A = 11.5% H2, 469 ppm CO, 47.9% CH4, 100 ppm C2H6, 31.1% C2H4, 309 ppm C3H8, 8.21% C3H6, 3367 ppm PD, 4042 ppm C2H2, 5287 ppm MA
B = 13.4% H2, 383 ppm CO, 46.4% CH4, 102 ppm C2H6, 31.6% C2H4, 314 ppm C3H8, 8.3% C3H6, 720 ppm PD, 2455 ppm MA
C = 7375 ppm H2, 38.7% CH4, 155 ppm C2H6, 47.9% C2H4, 479 ppm C3H8, 12.5% C3H6, 491 ppm PD, 1709 ppm MA
ND = Not detected
Y = G-83A catalyst, ⅛" Tabs
Z = G-55B catalyst, 3 × 6 spheres From reviewing the above results, it can surprisingly be seen that substantially low levels of propadiene can be obtained in the effluent from the third reactor, while still reducing ethylene loss with a relatively high space velocity being maintained in accordance with the present invention. Additionally, these results are unexpectedly obtained with relatively mild conditions in the third reactor thus eliminating concern of reaction runaway.

Many variations of the present invention will suggest themselves to those skilled in the art in light of the above-detailed description. For example, any of the known hydrogenation catalysts can be employed. Further, the hydrogenation reactors can be of the fixed bed type or other configurations useful in selective hydrogenation processes. Silver salts other than silver nitrate may be employed in chemically selectively absorbing olefins from olefin/paraffin gaseous mixtures.

In retrofit embodiments, a parallel cracked gas recovery system of the present invention may be added to the existing conventional separation system to expand total capacity. In general, in an expansion case, some of the existing equipment would be retrofitted (e.g., gas compressor, caustic system, cracked gas dryers) and some equipment added as new (e.g., front end initial partial hydrogenation reactors, partial demethanization system, finishing hydrogenation reactor, absorber/stripper system, olefin compressor and deethylenizer). All such obvious modifications are within the full intended scope of the appended claims.

All of the above-referenced patents, patent applications and publications are hereby incorporated by reference.

What is claimed is:

1. A process for hydrogenating acetylenes and dienes in a gas stream comprising ethylene, propylene, hydrogen, methane, ethane, acetylene, methyl acetylene and propadiene, said process comprising the steps of:
    (a) partially hydrogenating said gas stream to hydrogenate essentially all of the acetylenes and reducing the propadiene content to less than about 500 ppmv to produce a partially hydrogenated gas stream;
    (b) partially demethanizing the partially hydrogenated gas stream to remove at least about 80% of the methane and reduce the hydrogen concentration to less than about 5000 ppmv to produce a partially demethanized stream; and
    (c) further hydrogenating said partially demethanized stream in a finishing reactor system to hydrogenate essentially all of the propadiene contained in said partially demethanized stream to produce a finished hydrogenated stream.

2. A process as defined in claim 1 wherein said partial hydrogenation step (a) reduces the propadiene content to less than about 200 ppmv.

3. A process as defined in claim 1 wherein said partial hydrogenation step (a) reduces the propadiene content to from about 200 to about 500 ppmv.

4. A process as defined in claim 1 wherein said partial demethanization step reduces the hydrogen concentration to from about 1000 to about 5000 ppmv.

5. A process as defined in claim 1 wherein all of the hydrogen for said further hydrogenation step (c) is contained in said partially demethanized stream.

6. A process as defined in claim 1 wherein said partial demethanization step (b) comprises partially demethanizing the partially hydrogenated gas stream to produce a partially demethanized bottoms stream having a hydrogen concentration of from about 1000 ppmv to about 1 ppmv and a hydrogen containing overhead stream.

7. A process as defined in claim 6 further comprising supplying said finishing reactor system with a portion of said hydrogen containing overhead stream to provide the hydrogen required for said further hydrogenation step (c).

8. A process as defined in claim 1 wherein said partial demethanization comprises the steps of:
    (i) chilling said partially hydrogenated gas stream to a temperature ranging from about −30° C. to about −60° C. to partially condense out the $C_2^+$ components;
    (ii) separating the condensed $C_2^+$ components from the chilled gaseous stream;
    (iii) demethanizing said chilled gaseous stream to produce a fuel gas comprising primarily hydrogen and methane with small amounts of ethylene and ethane, and a bottoms stream comprising primarily $C_2^+$ components with small amounts of methane and hydrogen;
    (iv) expanding said fuel gas stream to provide refrigeration for the demethanization step;
    (v) flashing said bottoms stream and separating the flashed bottoms into a flashed vapor stream and a flashed liquid stream;
    (vi) combining the chilled liquid stream from step (ii) with the flashed liquid stream and vaporizing said combined stream; and
    (vii) compressing the flashed vapor stream and combining said compressed flashed vapor stream with said combined vaporized liquid stream to form said partially demethanized gas stream.

9. A process as defined in claim 1 wherein said propadiene concentration in said finished hydrogenated stream is less than about 50 ppmv.

10. A process as defined in claim 9 wherein said propadiene concentration in said finished hydrogenated stream is less than about 20 ppmv.

11. A process as defined in claim 1 wherein said finishing reactor system further reacts hydrogen with olefins to scavenge substantially all of the hydrogen.

12. A process as defined in claim 11 wherein the hydrogen concentration in said finished hydrogenated stream is less than about 10 ppmv.

13. A process as defined in claim 12 wherein the hydrogen concentration in said finished hydrogenated stream is less than about 1 ppmv.

14. A process for the recovery of olefins from a cracked gas stream comprising ethylene, propylene, hydrogen, methane, ethane, acetylenes, dienes and heavier hydrocarbons, said process comprising the steps of
   (a) partially hydrogenating said cracked gas stream to hydrogenate essentially all of the acetylenes and reducing the propadiene content to less than about 500 ppmv to produce a partially hydrogenated gas stream;
   (b) partially demethanizing the partially hydrogenated gas stream to remove at least about 80% of the methane and reduce the hydrogen concentration to less than about 5000 ppmv to produce a partially demethanized stream;
   (c) further hydrogenating said partially demethanized stream to hydrogenate essentially all of the propadiene contained in said partially demethanized stream;
   (d) contacting said further hydrogenated stream with a solution of a metallic salt capable of selectively chemically absorbing the ethylene and propylene to produce a scrubbed paraffin-rich gaseous stream and a chemically absorbed olefin-rich liquid stream; and
   (e) recovering said olefins from said chemically absorbed olefin-rich liquid stream.

15. A process as defined in claim 14 wherein said partial hydrogenation step (a) reduces the propadiene content to less than about 300 ppmv.

16. A process as defined in claim 14 wherein said partial hydrogenation step (a) reduces the propadiene content to from about 200 to about 300 ppmv.

17. A process as defined in claim 14 wherein said partial demethanization step reduces the hydrogen concentration to from about 1000 to about 5000 ppmv.

18. A process as defined in claim 15 wherein said process comprises compressing said cracked gas stream prior to said partial hydrogenation step.

19. A process as defined in claim 18 wherein said compression step comprises compressing said cracked gas stream to a pressure ranging from about 250 psig to about 400 psig.

20. A process as defined in claim 18 further comprising caustic washing the compressed cracked gas stream prior to partial hydrogenation to at least substantially remove any acid gases contained in said compressed cracked gas stream.

21. A process as defined in claim 15 further comprising drying the caustic washed compressed cracked gas stream prior to partial hydrogenation to at least substantially remove any water contained in said caustic washed compressed cracked gas stream.

22. A process as defined in claim 21 further comprising depropanizing the dried caustic washed compressed cracked gas stream prior to partial hydrogenation to at least substantially remove all of the $C_4$ and heavier hydrocarbons from said dried caustic washed compressed cracked gas stream.

23. A process as defined in claim 15 wherein olefin recovery step (e) comprises the steps of:
   (i) stripping said chemically absorbed olefin-rich liquid stream in an olefin stripper to produce a stripped gas stream rich in olefins and a lean liquid stream; and
   (ii) separating said stripped gas stream rich in olefins into an ethylene-rich product stream and a propylene-rich product stream.

24. A process as defined in claim 15 wherein said scrubbing solution comprises an aqueous solution of heavy metal ions selected from the group consisting of copper(I), silver (I), platinum(II) and palladium(II).

25. A process as defined in claim 24 wherein said scrubbing solution comprises a solution of aqueous silver nitrate.

26. A process as defined in claim 15 wherein said contacting step (d) is performed in an absorber tower, and said absorber tower comprises an upper water wash section for washing said scrubbed gaseous stream to remove residual scrubbing solution.

27. A process as defined in claim 23 wherein said olefin stripper comprises an upper water wash section for washing said stripped gas stream rich in olefins to remove residual scrubbing solution.

28. A process as defined in claim 23 further comprising recovering and recycling said lean liquid stream as said scrubbing solution.

29. A process as defined in claim 28 wherein said recovery and recycling comprises recovering the lean liquid stream from said stripper, passing at least a portion of said lean liquid stream through a reclaimer to decompose any acetylides formed from residual acetylenes, and recycling at least a portion of the reclaimed liquid stream as said scrubbing solution.

30. A process as defined in claim 23 wherein said step of separating ethylene from propylene comprises compressing said stripped gas stream rich in olefins to produce a compressed stripped gas stream rich in olefins, drying said compressed stripped gas stream rich in olefins to produce a dried compressed stripped gas stream rich in olefins and separating said dried compressed stripped gas stream rich in olefins in a deethylenizer tower into an ethylene-rich product stream and a propylene-rich product stream.

31. A process as defined in claim 23 wherein said step of separating ethylene from propylene comprises drying said stripped gas stream rich in olefins to produce a dried stripped gas stream rich in olefins, separating said dried stripped gas stream rich in olefins in a deethylenizer to tower to produce an overhead product stream rich in ethylene and a bottoms product stream rich in propylene, compressing said ethylene product stream, removing a portion of said propylene product stream for reboiling, and employing said compressed ethylene product stream as an indirect heat source for said deethylenizer reboiler.

32. A process as defined in claim 14 wherein said propadiene concentration in said further hydrogenated stream is less than about 50 ppmv.

33. A process as defined in claim 32 wherein said propadiene concentration in said further hydrogenated stream is less than about 20 ppmv.

34. A process as defined in claim 14 wherein said finishing reactor system further reacts hydrogen with olefins to scavenge substantially all of the hydrogen.

35. A process as defined in claim 34 wherein the hydrogen concentration in said further hydrogenated stream is less than about 10 ppmv.

36. A process as defined in claim 35 wherein the hydrogen concentration in said further hydrogenated stream is less than about 1 ppmv.

37. A process for debottlenecking and/or retrofitting an existing olefins recovery process comprising removing at least a portion of a dried, essentially acid gas free and compressed cracked gas stream comprising ethylene, propylene, hydrogen, methane, ethane, acetylenes, dienes and heavier hydrocarbons, and processing said removed gas stream in an olefin recovery process comprising the steps of:

(i) depropanizing said removed gas stream to at least substantially remove all of the $C_4$ and heavier hydrocarbons from said removed gas stream to produce a depropanized removed gas stream;

(ii) selectively partially hydrogenating said depropanized gas stream to hydrogenate essentially all of the acetylene and methyl acetylene and reducing the propadiene content to less than about 500 ppmv to produce a partially hydrogenated gas stream;

(iii) partially demethanizing said partially hydrogenated removed gas stream to remove at least about 80% of said methane and reduce the hydrogen concentration to less than about 5000 ppmv to produce a partially demethanized gas stream;

(iv) further hydrogenating said partially demethanized stream in a finishing reactor to hydrogenate essentially all of the propadiene in said partially demethanized stream;

(v) contacting said further hydrogenated gas stream with a solution of a metallic salt capable of selectively chemically absorbing the ethylene and propylene to produce a scrubbed paraffin-rich gaseous stream and a chemically absorbed olefin-rich liquid stream; and (vi) recovering said olefins from said metallic chemical absorbent solution.

38. A process as defined in claim 37 wherein all of the hydrogen for said further hydrogenation step (c) is contained in said partially demethanized stream.

39. A process as defined in claim 37 wherein said partial demethanization step (b) comprises partially demethanizing the partially hydrogenated gas stream to produce a partially demethanized bottoms stream having a hydrogen concentration of from about 1000 ppmv and a hydrogen containing overhead stream.

40. A process as defined in claim 39 further comprising supplying said finishing reactor system with a portion of said hydrogen containing overhead stream to provide the hydrogen required for said further hydrogenation step (c).

* * * * *